United States Patent
Sengun et al.

(10) Patent No.: US 12,011,155 B2
(45) Date of Patent: Jun. 18, 2024

(54) DOUBLE ROW COLLAPSIBLE SUTURE CONSTRUCT

(71) Applicant: Medos International Sarl, Le Locle (CH)

(72) Inventors: Mehmet Ziya Sengun, Canton, MA (US); Joseph Algeri, Burlington, MA (US)

(73) Assignee: Medos International Sarl, Le Locle (CH)

( * ) Notice: Subject to any disclaimer, the term of this patent is extended or adjusted under 35 U.S.C. 154(b) by 171 days.

(21) Appl. No.: 17/734,646

(22) Filed: May 2, 2022

(65) Prior Publication Data

US 2022/0257234 A1 Aug. 18, 2022

Related U.S. Application Data (62) Division of application No. 16/831,219, filed on Mar. 26, 2020, now Pat. No. 11,337,687.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 17/0469* (2013.01); *A61B 2017/0496* (2013.01); *A61F 2002/0852* (2013.01)

(58) Field of Classification Search
CPC .................. A61B 17/0401; A61B 2017/0496
See application file for complete search history.

(56) References Cited

U.S. PATENT DOCUMENTS

| | | | |
|---|---|---|---|
| 5,964,783 A | 10/1999 | Grafton et al. |
| 6,296,659 B1 | 10/2001 | Foerster |
| 6,641,597 B2 | 11/2003 | Burkhart et al. |
| 7,217,279 B2 | 5/2007 | Reese |

(Continued)

FOREIGN PATENT DOCUMENTS

WO 2017189096 A1 11/2017

OTHER PUBLICATIONS

Extended European Search Report received for EP Application No. 21164905.8, dated Aug. 24, 2021, 8 pages.

(Continued)

*Primary Examiner* — Phong Son H Dang
(74) *Attorney, Agent, or Firm* — Mintz Levin Cohn Ferris Glovsky and Popeo, P.C.

(57) ABSTRACT

Tissue fixation and repair constructs and methods of repair using the same are provided. An exemplary tissue fixation and repair construct can include a first implantable anchor coupled to a suture having a fixed tail and a tensioning tail. The fixed tail can include an overhand knot located distally adjacent to the finger trap, such that the overhand knot substantially abuts the finger trap when adjacent thereto, a fixed stopper knot configured to prevent further movement of the fixed tail through a second implantable anchor when the second implantable anchor is placed onto the suture, and a finger trap. The tensioning tail can be passed through the finger trap and overhand knot, and can be used to adjust the tension of the tissue fixation and repair construct when the first implantable anchor and the second implantable anchor are inserted into bone.

7 Claims, 11 Drawing Sheets

(56) References Cited

U.S. PATENT DOCUMENTS

| | | | |
|---|---|---|---|
| 7,226,469 B2 | 6/2007 | Benavitz et al. | |
| 7,285,124 B2 | 10/2007 | Foerster | |
| 7,601,165 B2 * | 10/2009 | Stone | A61B 17/0482 |
| | | | 606/232 |
| 8,366,744 B2 | 2/2013 | Bojarski et al. | |
| 8,764,797 B2 | 7/2014 | Dreyfuss et al. | |
| 8,840,643 B2 | 9/2014 | Dreyfuss | |
| 9,107,653 B2 | 8/2015 | Sullivan | |
| 9,179,905 B2 | 11/2015 | Pamichev et al. | |
| 9,301,745 B2 | 4/2016 | Dreyfuss | |
| 9,314,241 B2 | 4/2016 | Stone et al. | |
| 9,332,979 B2 | 5/2016 | Sullivan et al. | |
| 9,345,567 B2 | 5/2016 | Sengun | |
| 9,463,011 B2 | 10/2016 | Dreyfuss et al. | |
| 9,463,013 B2 | 10/2016 | Pilgeram et al. | |
| 9,687,222 B2 | 6/2017 | Dreyfuss et al. | |
| 9,763,655 B2 | 9/2017 | Sengun | |
| 9,788,838 B2 | 10/2017 | McClellan et al. | |
| 9,855,029 B2 | 1/2018 | Sullivan | |
| 9,867,607 B2 * | 1/2018 | Sullivan | A61B 17/0487 |
| 9,924,939 B1 | 3/2018 | Anderson | |
| 10,188,378 B2 | 1/2019 | Lunn et al. | |
| 10,603,028 B2 | 3/2020 | Sengun et al. | |
| 11,337,687 B2 | 5/2022 | Sengun et al. | |
| 2007/0219558 A1 * | 9/2007 | Deutsch | A61B 17/0401 |
| | | | 606/326 |
| 2008/0082127 A1 | 4/2008 | Stone et al. | |
| 2009/0082805 A1 * | 3/2009 | Kaiser | A61B 17/06166 |
| | | | 606/228 |
| 2009/0312776 A1 * | 12/2009 | Kaiser | A61F 2/0811 |
| | | | 606/228 |
| 2010/0256677 A1 | 10/2010 | Albertorio et al. | |
| 2010/0268273 A1 | 10/2010 | Albertorio et al. | |
| 2011/0208239 A1 | 8/2011 | Stone et al. | |
| 2011/0238111 A1 | 9/2011 | Frank | |
| 2012/0130423 A1 | 5/2012 | Sengun et al. | |
| 2012/0130424 A1 | 5/2012 | Sengun et al. | |
| 2013/0296895 A1 | 11/2013 | Sengun | |
| 2013/0296931 A1 * | 11/2013 | Sengun | A61B 17/06166 |
| | | | 606/228 |
| 2013/0296934 A1 * | 11/2013 | Sengun | A61B 17/06166 |
| | | | 606/232 |
| 2014/0277132 A1 * | 9/2014 | Sengun | A61B 17/0469 |
| | | | 606/232 |
| 2015/0066081 A1 * | 3/2015 | Martin | A61B 17/06166 |
| | | | 606/228 |
| 2017/0049431 A1 | 2/2017 | Dooney, Jr. | |
| 2017/0049434 A1 | 2/2017 | Dooney, Jr. et al. | |
| 2017/0105716 A1 | 4/2017 | Burkhart | |
| 2017/0119382 A1 | 5/2017 | Denham et al. | |
| 2017/0128063 A1 | 5/2017 | Jackson | |
| 2018/0353166 A1 | 12/2018 | Breslich | |
| 2018/0353167 A1 | 12/2018 | Lombardo et al. | |
| 2018/0360437 A1 | 12/2018 | Sengun et al. | |
| 2020/0268502 A1 * | 8/2020 | Brunsvold | A61F 2/0811 |

OTHER PUBLICATIONS

U.S. Appl. No. 16/831,219, filed Mar. 26, 2020, Double Row Collapsible Suture Construct.

* cited by examiner

DOUBLE ROW COLLAPSIBLE SUTURE CONSTRUCT

CROSS-REFERENCE

The present application is a divisional of U.S. patent application Ser. No. 16/831,219 entitled "Double Row Collapsible Suture Construct," filed Mar. 26, 2020.

BACKGROUND

A variety of injuries and conditions require repair of soft tissue damage, or reattachment of soft tissue to bone and/or surrounding tissue. For example, when otherwise healthy tissue has been torn away from a bone, such as a shoulder rotator cuff tendon being partially or completely torn from a humerus (a rotator cuff tear), surgery is often required to reattach the tissue to the bone, to allow healing and a natural reattachment to occur. A number of devices and methods have been developed for performing these surgical repairs. Some of the more successful methods including the use of suture fixation members, such as suture anchors, which typically include an anchor body having one or more suture attachment feature and include a tissue or bone engaging feature for retaining the suture anchor within or adjacent to the tissue or bone. Depending on the specific injury, one or more suture anchors connected to, or interconnected by, one or more segment of suture, may be used to perform the repair.

Surgery can also be required when a tear occurs in the substance of a single type of tissue. Sutures can also be used in conjunction with one or more suture anchors to repair such tissue tears. Sutures can be fastened to suture anchors and to tissue using knots tied by the surgeon during a repair procedure, or using "knotless" devices and methods, where one or more anchors and one or more sutures can be connected and tensioned without the surgeon needing to tie knots during the surgery. Knotless anchoring is of particular utility for minimally invasive surgeries, such as endoscopic or arthroscopic repairs, where the surgeon remotely manipulates the suture at the surgical site using tools inserted through a small diameter cannula or endoscopic tube, which can make the knotting process difficult and tedious.

However, current techniques for double-row fixation require the tension of the suture to be set while the anchor is inserted, and as such it can be difficult to reliably set the correct amount of tension. In addition, current techniques require the use of multiple anchors for both medial and lateral rows. Furthermore, with current techniques and fixation device designs, the suture retention capacity for a lateral row anchor is relatively low, as the suture is often compressed between the bone and the anchor.

Accordingly, there remains a need for improved tissue repair devices, systems, and methods.

SUMMARY

In an aspect, a tissue repair construct is provided and can include a first implantable anchor and a flexible member. The first implantable anchor can include an engagement member and at least one bone engaging feature on an outer sidewall of the first implantable anchor. The flexible member can include an intermediate portion coupled to the engagement member, and first and second tails extending from the intermediate portion. Each of the first and second tails can include a terminal end. A portion of the first tail can extend through an interior collapsible passage formed in a portion of the second tail and a first knot formed in the second tail adjacent to the hollow portion. The second tail can include a fixed knot intermediate the first knot and the terminal end of the second tail.

In some embodiments, the intermediate portion can be slidably coupled to the engagement member. In other embodiments, the tissue repair construct can include a second implantable anchor configured to be coupled to the second tail. In such embodiments, the second implantable anchor can be disposed proximate the fixed knot. In yet other embodiments, the terminal end of the first tail can be configured to be coupled to the second tail. In still other embodiments, the terminal end of the first tail is configured to be separated from the second tail. In some embodiments, the distance between the fixed knot and the first knot can be disposed at a distance from the fixed knot, the distance approximately equal to 3-5 mm more than a length of the first implantable anchor. In other embodiments, the interior collapsible passage can be configured to be disposed outside of a bone when the first implantable anchor is disposed in the bone.

In another aspect, a method is provided. The method can include inserting a tissue repair construct into a first bone hole, the tissue repair construct including a first implantable anchor having an engagement member and at least one bone engaging feature on an outer sidewall thereof, and a flexible member coupled to the engagement member and at least one tail extending therefrom, wherein the flexible member is spliced to itself to form a loop proximal to the first implantable anchor; passing at least a portion of the flexible member through or around soft tissue; coupling the flexible member to a second implantable anchor; inserting the second implantable anchor and at least a portion of the flexible member into a second bone hole; and tensioning the flexible member after the second implantable anchor is inserted into the second bone hole so as to apply and set a desired amount of tension in the repair construct.

In some embodiments, the flexible member can have an intermediate portion coupled to the engagement member with first and second tails extending therefrom, each of which has a terminal end and wherein the flexible member is spliced by passing the first tail through a portion of the second tail. In such an embodiment, the method can include, following the passing step, separating the terminal end of the first tail from the second tail and coupling the flexible member to the second anchor by inserting the terminal end of the second tail into the second implantable anchor. In other embodiments, a distal end of the flexible member can be coupled to the first implantable anchor, and the second anchor can be coupled to the second implantable anchor by coupling the loop in the flexible member to a coupling suture attached to the second implantable anchor.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. Additionally, although terms such as "first" and "second" are used to describe various aspects of a component, e.g., a first end and a second end, such use is not indicative that one component comes before the other. Use of terms of this nature may be used to distinguish two similar components or features, and often such first and second components can be used interchangeably. Still further, a number of terms may be used throughout the disclosure interchangeably but will be understood by a person skilled in the art.

Soft tissue fixation and repair constructs and methods of soft tissue repair using the same, and kits including the same are provided. These constructs are particularly useful in double-row fixation repair, e.g., for rotator cuff repair, and include an implantable anchor that has coupled thereto a collapsible loop. After the anchor is implanted into bone, such as on the medial side, and the flexible member is passed through or around soft tissue, the flexible element can be coupled to a second implantable anchor, such as a knotless anchor for a lateral row, and the second anchor is implanted into bone. Among the advantages of the construct described herein is the fact that tension can be applied to the flexible member to tighten the flexible loop through a knotless technique and compress the soft tissue to bone after the anchors are inserted into bone. A drawback of many current techniques is that tension can only be applied while the second anchor is being inserted, thus making it difficult to control tension. The soft tissue fixation and repair constructs and methods of soft tissue repair described herein provide for stronger lateral row fixation through a more convenient and less time consuming procedure. A further advantage of the constructs and techniques disclosed herein is the ability to use the same type of anchor for both the medial and lateral rows, which is typically not the case in current practice.

Figure 1:
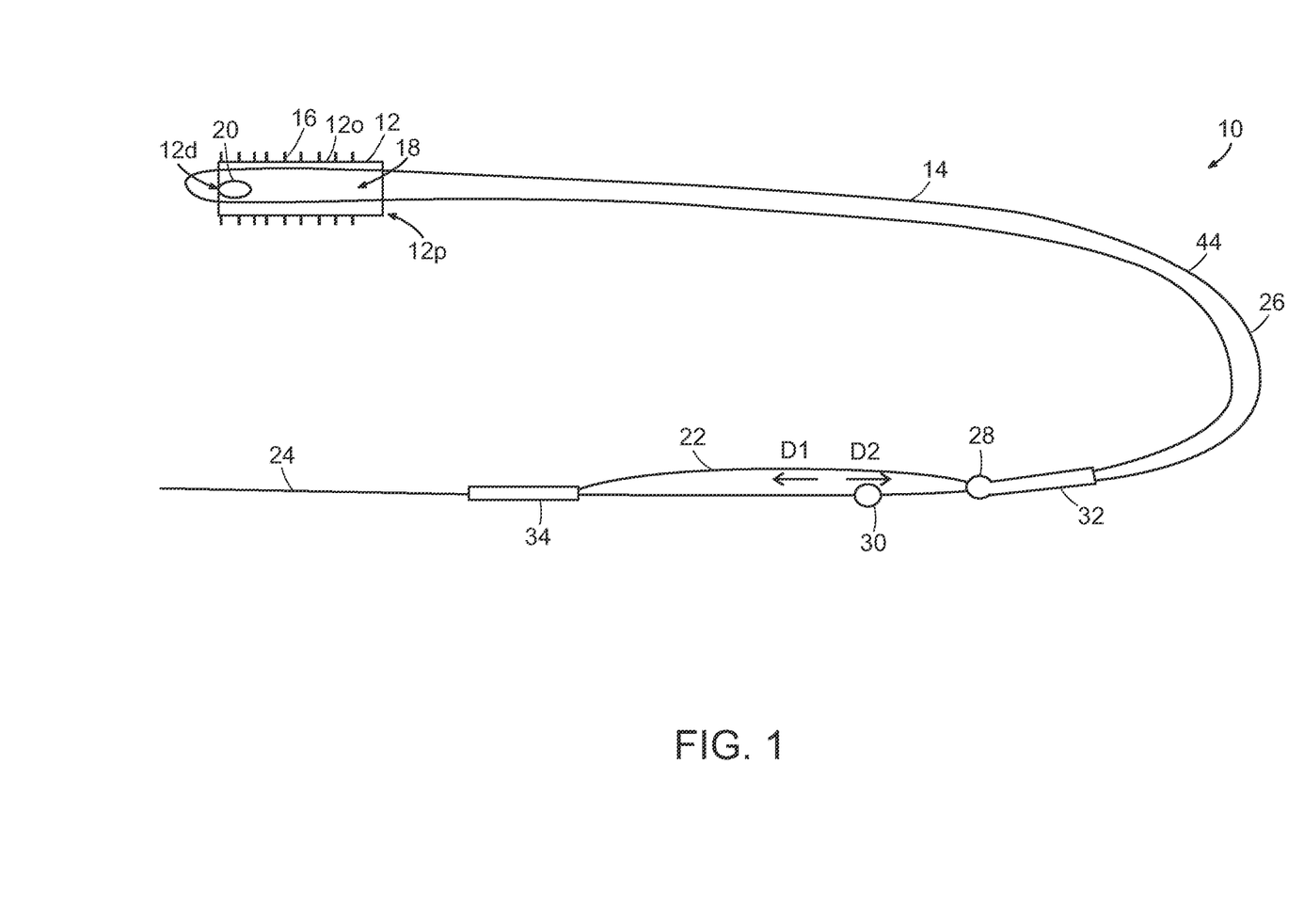
FIG. 1 is a schematic view of one embodiment of a tissue fixation and repair construct.

FIG. 1 illustrates one embodiment of a tissue fixation and repair construct 10 configured to be implanted in a body of a patient to facilitate soft tissue repair. The tissue fixation and repair construct 10 includes a first implantable anchor 12, such as a medial anchor that is configured to be inserted into a hole that has been formed in bone, with a flexible member 14 coupled thereto. In an exemplary embodiment the first implantable anchor 12 has at least one bone engaging feature 16 located on an outer sidewall thereof. Further, in some implementations, the first implantable anchor 12 is cannulated, having a lumen 18 extending therethrough, with a first flexible member engagement feature 20 spanning the lumen 18 at a distal end 12d of the implantable anchor 12. The flexible member can include a first tail 22, a second tail 24, and an intermediate portion 26 disposed between the first tail 22 and the second tail 24. The first tail 22 can be a tensioning tail that can be used by a surgeon to adjust the overall tension of the flexible member 14 during installation of the tissue fixation and repair construct 10. The second tail 24 can be a fixed tail upon which various features can be formed, such as an overhand knot 28, a fixed stopper knot 30, and a finger trap 32, each of which is discussed in further detail below. The first tail 22 and the second tail 24 can optionally be coupled together by a terminating splice 34.

Figure 2A:
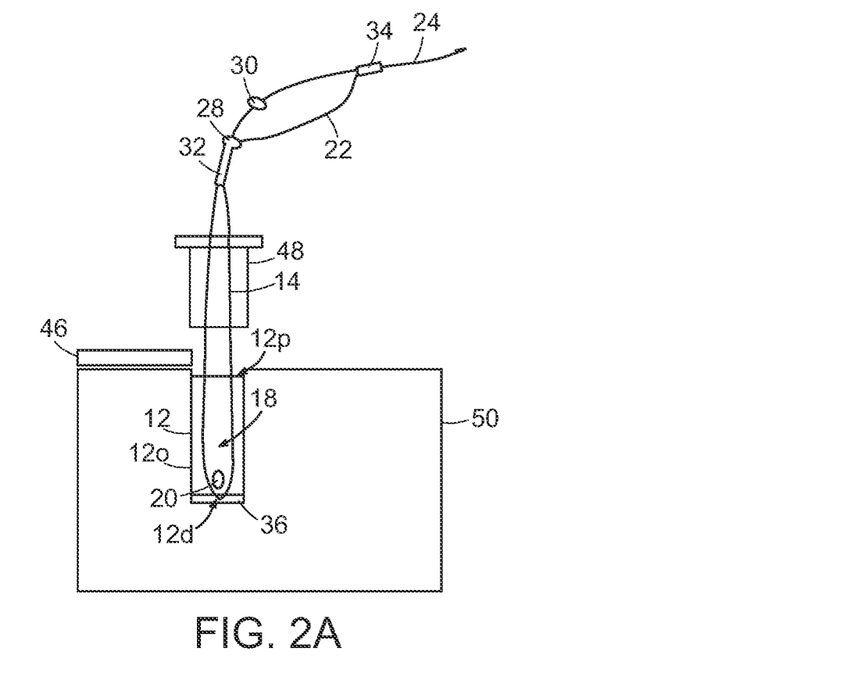
FIG. 2a is a side cross-sectional schematic view of the tissue fixation and repair construct of FIG. 1 during an initial step of a surgical procedure in which a first implantable anchor is inserted into a hole formed in bone.
Figure 2B:
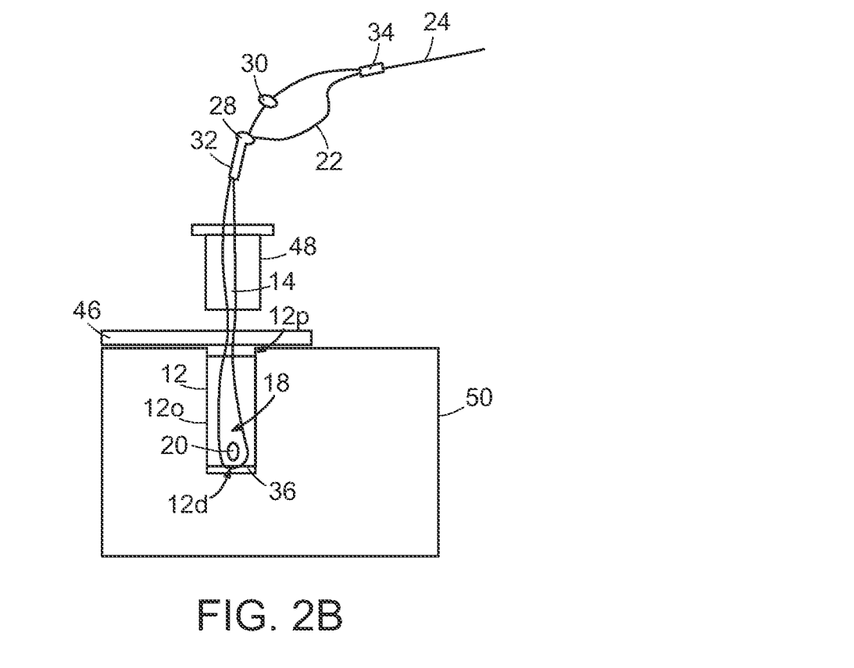
FIG. 2b is a side cross-sectional schematic view of the tissue fixation and repair construct of FIG. 1 during a subsequent step in a surgical procedure in which a portion of the construct is passed through a soft tissue.
Figure 2C:
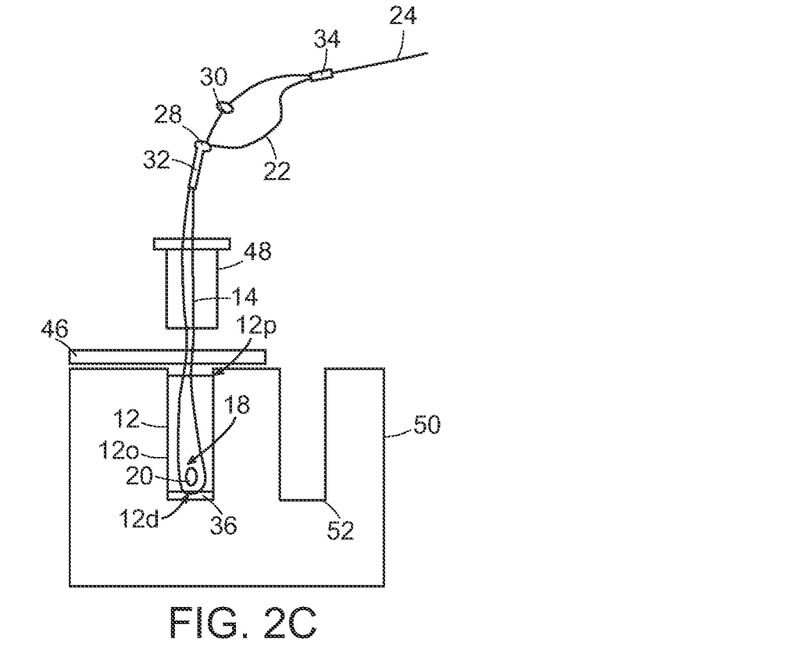
FIG. 2c is a side cross-sectional schematic view of the tissue fixation and repair construct of FIG. 1 during a subsequent step in a surgical procedure in which a second hole is formed in bone.
Figure 2D:
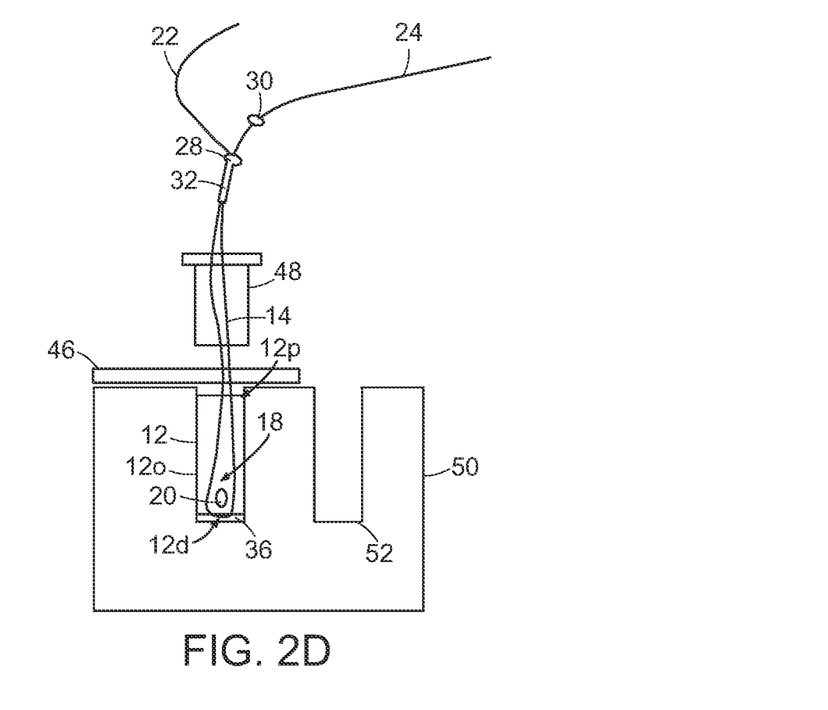
FIG. 2d is a side cross-sectional schematic view of the tissue fixation and repair construct of FIG. 1 during a subsequent step in a surgical procedure in which a tensioning tail of a flexible member is separated from a fixed tail of the tensioning member.
Figure 2E:
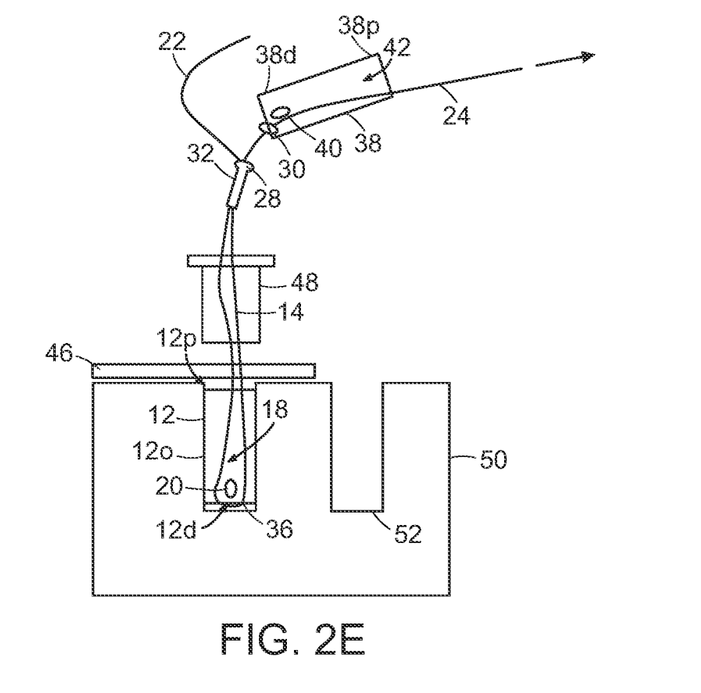
FIG. 2e is a side cross-sectional schematic view of the tissue fixation and repair construct of FIG. 1 during a subsequent step in a surgical procedure in which the fixed tail is coupled with a second anchor to be implanted in the second hole.
Figure 2F:
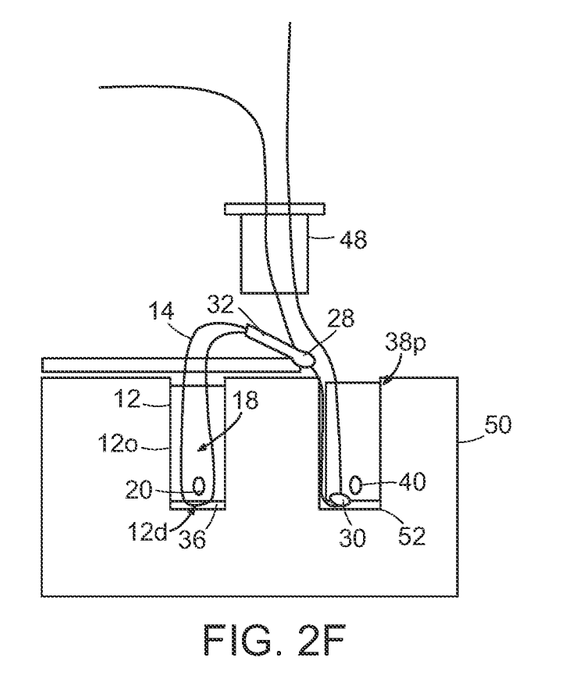
FIG. 2f is a side cross-sectional schematic view of the tissue fixation and repair construct of FIG. 1 during a subsequent step in a surgical procedure in which the second anchor is implanted into the second hole.
Figure 2G:
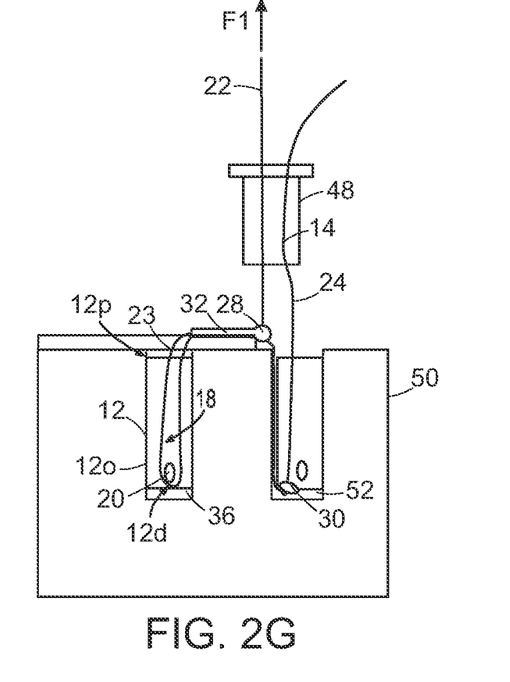
FIG. 2g is a side cross-sectional schematic view of the tissue fixation and repair construct of FIG. 1 during a subsequent step in a surgical procedure in which the tensioning tail is tensioned to approximate the soft tissue to bone.

As shown in FIGS. 1-2g, the tissue fixation and repair construct includes a first implantable anchor 12 that is configured to be implanted in bone in a secure manner. In such constructs, the implantable anchor is configured to couple to a suture and to be used in a tissue repair procedure, e.g., for soft tissue reattachment or repair at a joint such as the hip, knee, or shoulder, and in particular a rotator cuff repair procedure.

One skilled in the art will appreciate that a variety of suture anchor types can be used in conjunction with the constructs provided herein, including both hard and soft anchors, and including screw-type anchors, and that the disclosure is not intended to be limited to the designs of anchors provided for herein. Some exemplary embodiments of anchors that can be used in conjunction with the constructs and related teachings provided for herein include a Healix Ti™ anchor, a Healix Advance™ anchor, a Healix Advance™ Knotless anchor, a Versalok™ anchor, and a Gryphon™ anchor, each of which is commercially available from DePuy Mitek Inc., 325 Paramount Drive, Raynham, Mass. 02767, as well as anchors described in U.S. Pat. No. 9,345,567, entitled "Systems, Devices, and Methods for Securing Tissue Using Snare Assemblies and Soft Anchors" and U.S. Pat. No. 9,763,655, entitled "Systems, Devices, and Methods for Securing Tissue Using Hard Anchors," the content of each of which is incorporated by reference herein in their entireties. One skilled in the art will further appreciate that the implantable anchors can be made from a variety of well-known materials, including those that are absorbable and non-absorbable. Further, the implantable anchors can have any of a variety of sizes as appropriate for use at a particular anatomical location and with a particular patient.

The suture anchors described herein are configured to maintain engagement with a flexible member, such as a suture material. As shown in FIGS. 1-2g, for example, the first implantable anchor 12 has a proximal end 12p and a distal end 12d disposed opposite the proximal end 12p. The distal end 12d of the first implantable anchor 12 is configured to be inserted into a hole formed in bone, such as first bone hole 36. The first implantable anchor is cannulated and, as such, has a lumen 18 extending therethrough from the proximal end to the distal end. As shown, the lumen 18 is cylindrically shaped, however a variety of lumen shapes are possible. The first implantable anchor 12 can also include a flexible member engagement feature 20 that spans across the lumen 18 at the distal end 12d and that is configured to retain a portion of the flexible member 14 in engagement with the suture anchor and disposed within the lumen 18. Alternatively, the anchor 12 need not have a lumen 18, but can have the flexible engagement feature 20 at the proximal end 12p, or it may include a proximal eyelet to engage with the flexible member 14. An exemplary embodiment of such an anchor, which can be used in conjunction with the constructs and relating teachings provided for herein, include a Spiralok anchor, which is commercially available from DePuy Mitek, Inc.

The suture anchors also include at least one feature to facilitate secure engagement in bone. By way of example, first implantable anchor 12 includes bone engaging features 16 formed on an outer sidewall thereof and configured to engage with the first bone hole 36 and thereby secure the first implantable anchor 12 in place. As shown in FIG. 1, in some implementations, the bone engaging feature 16 can comprise a plurality of protrusions that extend from an outer sidewall 12o of the first implantable anchor 12. The protrusions can be in the form of barbs and/or threads, or any similar structure that enables the anchor to obtain purchase with bone and remain securely attached to bone.

The flexible member 14 of the tissue fixation and repair construct 10 can be a filament or suture material, such as a suture thread and/or a suture tape. One skilled in the art will appreciate that the filament or suture material can be any type and material typically used as filament, including a cannulated filament, a braided filament, and a mono filament. The type and strength of the filament can depend, at least in part, on the other components with which the construct is used, such as the suture anchor, the tissue through which it will be passed or coupled to, and the type of procedure in which it is used. In some embodiments the filament can have a size between about a #5 filament (about 20 gauge to about 21 gauge) and about a #5-0 filament (about 35 gauge to about 38 gauge), and in one exemplary embodiment the filament is a #2 filament (about 22 gauge to about 24 gauge), such as an Orthocord™ filament that is commercially available from DePuy Mitek, Inc., or an Ethibond™ filament that is commercially available from Ethicon, Inc., Route 22 West, Somerville, N.J. 08876. The flexible member 14 can be any type of suture and can be made from a variety of well-known materials, including natural materials and synthetic materials. Examples of materials for the flexible member include polymers, such as polyglycolide, polypropylene, polyethylene terephthalate (PET), and polydioxanone, and fabrics, such as nylon and silk. The flexible member 14 can be bioabsorbable, partially bioabsorbable, or nonabsorbable, and can have a circular cross section or another cross section, such as square or rectangular. The flexible member 14 can also be hollow.

The thickness of the filament should provide strength in the connection but at the same time minimize the trauma caused to tissue through which it passes. In some embodiments, different portions of the tissue fixation and repair construct 10 can have different thicknesses, with the thickness being based, at least in part, on the purpose for that portion, the thicknesses of the other portions of the construct, the components or tissue through which that portion may be passed, and the type of procedure in which the construct is used. Orthocord™ suture is approximately 55 to 65 percent PDS™ polydioxanone, which is bioabsorbable, and the remaining 35 to 45 percent ultra-high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed.

The flexible member 14 can be formed from a single thread or from a plurality of threads. The plurality of threads can be coupled together to define a flexible member strand in any of a variety of ways, such as by being braided together. In an exemplary embodiment, the thread(s) that form the flexible member 14 are sufficiently flexible to allow the suture to be flexible. The threads that form the flexible member 14 can made from different materials, e.g., a first number of the threads being nylon and a second number of the threads being PET, or, all threads of the flexible member 14 can be made from the same material. A flexible member 14 formed from a plurality of threads can, in some embodiments, include a core around which the threads are arranged, such as by braiding. The core may provide the suture with strength to help prevent the suture from breaking, snapping, etc. The suture can have any of a variety of sizes, such as a size in a range of about size #5 to #5-0.

When applied to form the construct 10, and as shown in FIGS. 1-2g, the flexible member has a first tail 22, a second tail 24, and an intermediate portion 26 disposed between the first tail and the second tail. The first tail 22 can be a tensioning tail that can be used to adjust the tension of the suture during installation of the construct in a surgical procedure. The second tail 24 is a fixed tail that can include such features as an overhand knot, a fixed stopper knot, and a finger trap which are described in further detail below.

With continued reference to FIGS. 1-2g, the second tail 24 of the flexible member 14 has an overhand knot 28 formed thereon, which is located distally adjacent to the finger trap 32 relative to the first implantable anchor 12, such that the overhand knot 28 substantially abuts the finger trap 32. The overhand knot 28 is configured to help maintain the integrity of the finger trap 32, and to enable the first tail 22 to pass through the overhand knot 28 in such a way that the first tail 22 can be slidably moved through the overhand knot 28 in response to tension applied by a surgeon. A person skilled in the art will appreciate that although a small gap may exist between the overhand knot 28 and the finger trap 32 such that the overhand knot 28 does not abut the finger trap 32 so as to be in direct contact with the finger trap 32, the overhand knot 28 can nevertheless be considered to substantially abut the finger trap 32 due to any number of facts, such as manufacturing tolerance. Although the overhand knot 28 is shown and described as an overhand knot, which may be beneficial in surgical procedures due to its low profile, any type of knot known to one of ordinary skill in the art that is capable of achieving the functionality described herein may also be used in lieu of an overhand knot, such as a hitch knot. The overhand knot 28 is formed by the flexible member 14 itself. However, in other embodiments, another flexible member can be attached to the flexible member 14 to form the overhand knot 28 (e.g., tied around the flexible member 14 to form the overhand knot 28 thereon).

The second tail 24 of the flexible member 14 also has a fixed stopper knot 30 formed thereon. As explained in further detail below, the fixed stopper knot 30 is configured to maintain engagement between the flexible member 14, and particularly second tail 24, and thus prevent movement of the second tail 24 through a second implantable anchor 38 (shown in FIGS. 2e-2g). The second implantable anchor 38, as described in more detail below, can be the same type of suture anchor as the first implantable anchor 12, and thus have the same structures and features as the first implantable anchor 12. By way of example, the second implantable anchor 38 can be used in a lateral row of a double-row repair construct. Affixation of the second implantable anchor 38 to the flexible member 14 is described in more detail below in connection with a discussion of the method of using construct 10. In any event, to maintain engagement between the second tail 24 and the second implantable anchor 38, the diameter of the fixed stopper knot 30 should be greater than the space between the flexible member engagement feature 40 of second implantable anchor 38 and the wall of the lumen 42 of the second implantable anchor 38. This structure prevents the fixed stopper knot 30 from fully entering the second lumen 42 and thus the second tail 24 remains connected to the second implantable anchor 38.

The fixed stopper knot 30 is positioned on the second tail 24 at a particular location that is sufficiently spaced from the finger trap 32 and the overhand knot 28 such that operation of the finger trap 32 is not impeded and so that the finger trap remains spaced from the bone hole in which the second implantable anchor 38 is to be placed. A person skilled in the art will appreciate that this predetermined distance will vary depending on a variety of factors, including the size of the anchors used and the procedure and anatomy involved. Typically the predetermined distance is about 5-15 mm, and typically about 10 mm, greater than the length of the second implantable anchor 38.

The finger trap 32 useful with the construct 10 disclosed herein can take a variety of forms as long as it allows the tensioning tail 22 to pass therethrough. In general, the finger trap 32 is an area of the flexible member 14 that is hollow and through which the flexible member passes through itself. For example, the first tail 22, when under tension, is slidable uni-directionally in a first direction D1 through the finger trap 32 and is locked from sliding through the finger trap 32 in the other, opposite direction D2 because the tension collapses the finger trap 32 on the portion of the first tail 22 of the suture passing therethrough. Exemplary finger traps are described in detail in U.S. patent application Ser. No. 15/622,360 filed on Jun. 14, 2017 and entitled "Finger Traps for Collapsible Suture Loops," the disclosure of which is incorporated by reference herein in its entirety.

The flexible member 14 of the construct 10 defines an adjustable loop 44 that includes partial portions of each of the first tail 22 and the second tail 24, and the entirety of the intermediate portion 26. As previously mentioned, the flexible member 14 can be tensioned by a surgeon by pulling on the first tail 22 to slide a portion of the flexible member 14 through the finger trap 32. This tensioning collapses the adjustable loop 44 and reduces a distance between the finger trap 32 and the first implantable anchor 12.

An exemplary method of fixing soft tissue, such as a tendon 46, using the tissue fixation and repair construct 10 is described with reference to FIGS. 2a-2g. The method illustrated in FIGS. 2a-2g is performed in a minimally invasive manner, e.g., arthroscopically, through a cannula, such as cannula 48, that can be disposed through a patient's skin using techniques known to those skilled in the art. In the illustrated embodiment, the cannula is substantially aligned with the location at which the procedure is performed and serves as a working channel through which the tissue fixation and repair construct 10 and various tools required to perform the procedure are passed. A person skilled in the art will recognize other ways by which the procedures described herein can be performed, including through three or more cannulas, a single cannula, or through no cannula at all. Further, other types of procedures, such as open procedures, can be used in conjunction with the present disclosures, which may not require a cannula such as cannula 48.

FIG. 2a shows the tissue fixation and repair construct of FIG. 1, wherein the first implantable anchor 12 has been inserted into the first bone hole 36 that has been formed in a portion of a bone 50. A variety of commonly known tools and methods can be used to form the first bone hole 36, such as a drill. The first bone hole 36 can be disposed at a location proximate to the location at which the tendon 46 is to be attached to the bone 50. After the first bone hole 36 has been formed, the tissue fixation and repair construct 10 can then be passed through the cannula and implanted in the first bone hole 36 using ordinary techniques, such as by using a driver to screw or tap the anchor into place. As shown, the first tail 22 is coupled to the second tail 24 via the terminating splice 34 during the insertion. And while the anchor and the intermediate portion of the flexible member are disposed within the bone hole and the subject's body, the remainder of the construct 10 extends out of the subject's body and out of the cannula 48.

FIG. 2b shows the tissue fixation and repair construct of FIG. 1, wherein a portion of the flexible member 14 has been passed through the tendon 46 after the first implantable anchor 12 has been inserted into the first bone hole 36. As the end of the first tail 22 is coupled to the second tail 24 via the terminating splice 34, the number of separate tails passed through or around the tendon 46 and the cannula 48 can be reduced, and thus the passage of the flexible member 14 through the tendon 46 is simplified. While the first tail 22 and the second tail 24 can be passed through or around tissue such as tendon 46 using a number of techniques known to those skilled in the art, in some embodiments a suture passing device such as the EXPRESSEW II flexible suture passer, which is available from DePuy Mitek, LLC, can be passed through the cannula 46 and operated to pass the first tail 22 and the second tail 24 through the tendon 46.

Subsequently, a second bone hole 52 is then formed in a portion of bone 50 adjacent to first bone hole 36, as shown in FIG. 2c. This can be accomplished using tools and methods that are similar to or the same as those used to create the first bone hole 36. As will be explained in further detail below, the second bone hole 52 is configured to receive the second implantable anchor 38 that can be coupled to the tissue fixation and repair construct 10. The second implantable anchor 38 can be of the same type as or similar to the first implantable anchor, as shown in FIG. 2e. The end of the first tail 22 is separated from the second tail 24 after the portion of the flexible member 14 has been passed through the tendon 46, as shown in FIG. 2d.

The flexible member 14 is then coupled to the second implantable anchor 38 by inserting the second tail 24 into the second lumen 42 of the second implantable anchor 38, such that the second tail 24 extends into the distal end 38d of the second implantable anchor 38 toward a proximal end 38p of the second implantable anchor 38. In doing so, the fixed stopper knot 30 engages the flexible member engaging member 40 of the second implantable anchor 38, allowing the terminal portion of second tail 24 to pass through the proximal end 38p of second implantable anchor 38 while preventing passage therethrough of the fixed stopper knot 30 as shown in FIG. 2e. As the fixed stopper knot 30 has a larger diameter than the at least one passageway of the second implantable anchor, the fixed stopper knot 30 cannot pass through the at least one passageway of the second implantable anchor 38 and thus constrains the suture from extending further in the direction of the proximal end 38p of the second implantable anchor 38. A benefit of the fixed stopper knot 30 is that the position of the fixed tail can be maintained relative to the second implantable anchor 38, which significantly simplifies flexible member management while the second implantable anchor is passed through the cannula 48 and to the insertion site at the second bone hole 52.

After attaching the flexible member 14 to the second implantable anchor 38, the second implantable anchor 38 is then inserted into the second bone hole 52, distal end 38d first, as shown in FIG. 2f. As the fixed stopper knot 30 is constrained from passing proximally to flexible member engagement feature 20 of the second implantable anchor 38, it will be maintained in that position relative to the anchor. Thus, flexible member retention is not only provided by compression between the bone and the anchor, but also by the anchoring provided by the fixed stopper knot 30. Once the second implantable anchor 38 is positioned within bone hole 52, the terminal ends of first and second tails 22, 24 are positioned such that the extend through and out of cannula 48 so they are accessible to and able to be manipulated by a surgeon.

As shown in FIG. 2g, after the second implantable anchor has been inserted into the second bone hole 52, tension can be applied to the first tail 22 by a surgeon pulling on the terminal end of the first tail 22 in the direction of arrow F1. The action of the flexible member 14 sliding through the finger trap 32 collapses the adjustable loop 44 and compresses the tendon 46 against bone as a result of tensioning the portion of the construct connecting the first and second implantable anchors 12, 38. As the overhand knot 28 is designed to reduce stress on the flexible member 14 and the finger trap 32, the finger trap 32 is protected from damage in the event the direction of pull on the first tail 22 is at an oblique angle to the finger trap 32, or in a direction other than direction D1 as shown in FIG. 1. One particular advantage of the construct described herein is that the construct can be tensioned after the first and second anchors are implanted in bone, thus simplifying the procedure and enabling the desired amount of tension to be set (and maintained) after implantation. This advantage makes the construct described herein particularly suitable for use with knotless double-row repair constructs, and it enables the same type of anchor to be used for both the medial and lateral rows.

Following tensioning, the cannula is removed, excess suture material is trimmed and removed, and the surgical wound is closed.

Figure 3:
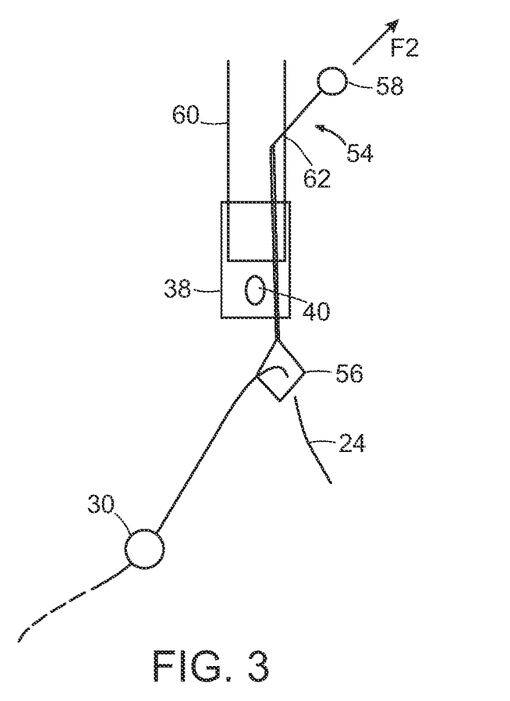
FIG. 3 is a side cross-sectional schematic illustration of an exemplary technique for coupling the flexible member of the tissue fixation and repair construct of FIG. 1 with the second anchor.

In some implementations, a threader, such as the threader 54 shown in FIG. 3, can be utilized by a surgeon to facilitate the insertion of the second tail 24 through the distal end 38d of the second implantable anchor 38 when the tissue fixation and repair construct 10 is being assembled at the surgical site. The threader 54 can include a coupling feature 56 at its distal end for engaging the first tail 22, and a handle 58 for grasping by a surgeon. In use, when the second implantable anchor 38 has been inserted through the cannula 48 via the use of a slotted inserter 60, the surgeon can pull on the handle 58 in the direction of arrow F2 and thereby pull the threader 54, through a slot 62 formed in the inserter 60, and thereby bring the fixed stopper knot 30 into contact with the flexible member engagement feature 40 of the second implantable anchor 38.

Figure 4:
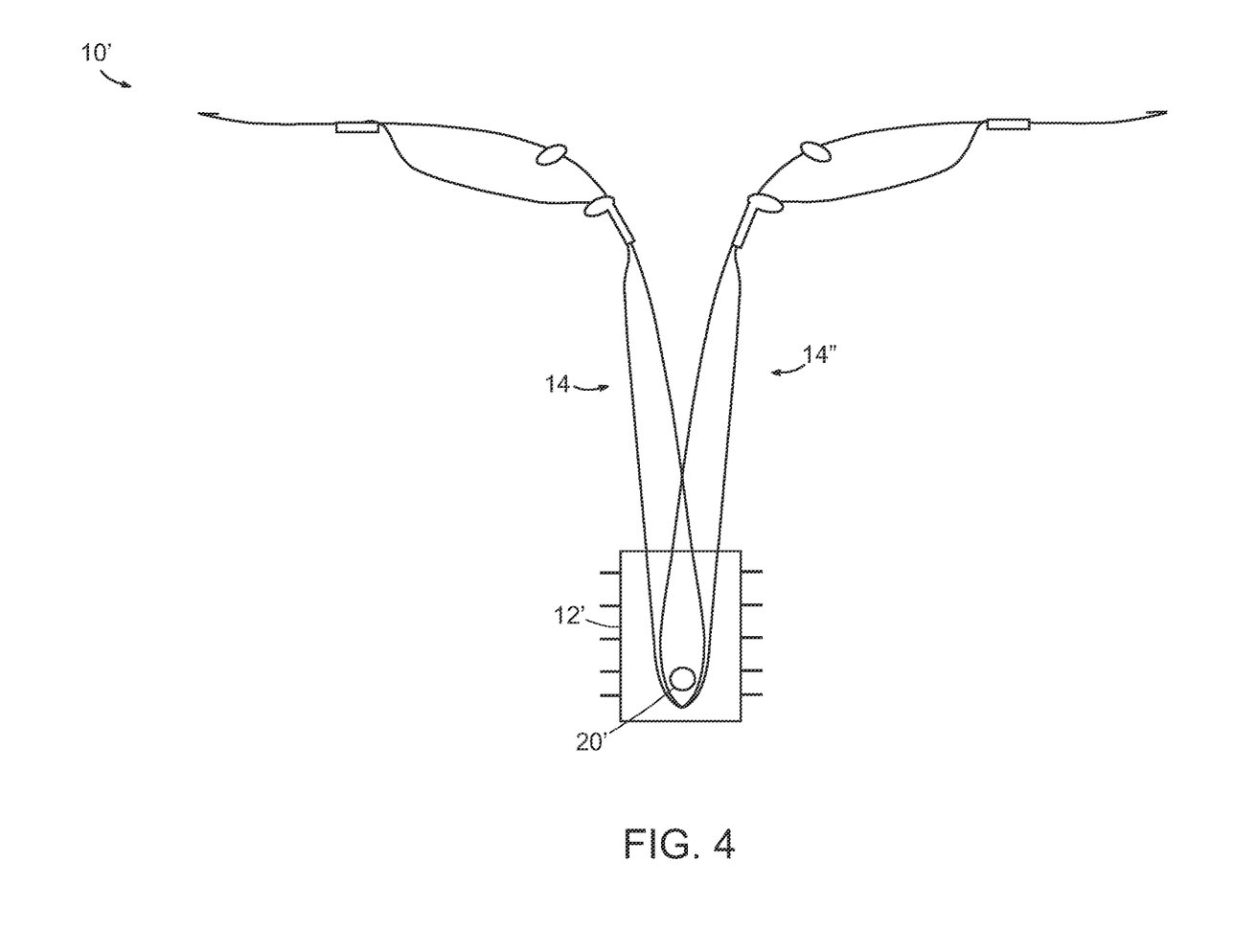
FIG. 4 is a side cross-sectional schematic view of an additional embodiment of a tissue fixation and repair construct having multiple flexible members coupled to an implantable anchor.

Although the method is described using a technique in which the first implantable anchor is loaded with a single flexible member that will connect to a single second implantable anchor, a person skilled in the art will appreciate that the first implantable anchor may be single, double, or triple loaded with collapsible sutures, each of which can be connected to a second implantable anchor. FIG. 4 illustrates an exemplary embodiment of a tissue fixation and repair construct 10' that includes a first implantable anchor 12' that is loaded with a first flexible member 14' and a second flexible member 14". As shown in this embodiment, the first and second flexible members 14', 14" are structurally the same as the flexible member 14 described above and illustrated in FIGS. 1-2g, and the first implantable anchor 12' is structurally the same as the first implantable anchor 12 (also described above and illustrated in FIGS. 1-2g). The flexible member 14 and the second flexible member 14' are each coupled to a flexible member engagement feature 20' of the first implantable anchor 12,' and are thereby retained in engagement with the first implantable anchor 12'.

Figure 5:
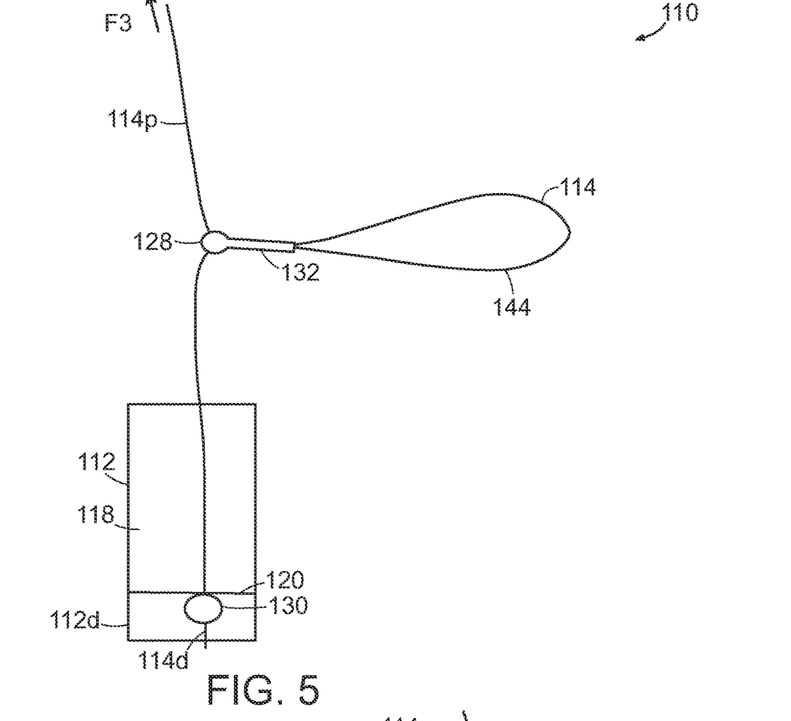
FIG. 5 is a side cross-sectional schematic view of one embodiment of a tissue fixation and repair construct.
Figure 6A:
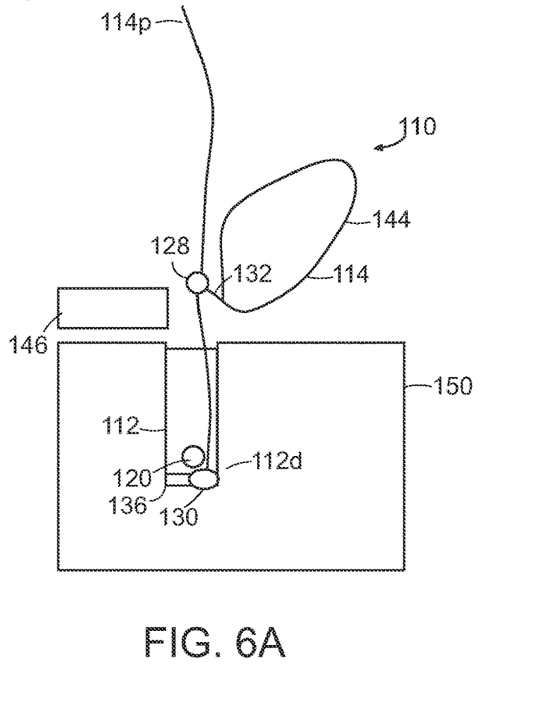
FIG. 6a is a side cross-sectional schematic view of the tissue fixation and repair construct of FIG. 5 during an initial step of a surgical procedure in which a first implantable anchor is inserted into a hole formed in bone.
Figure 6B:
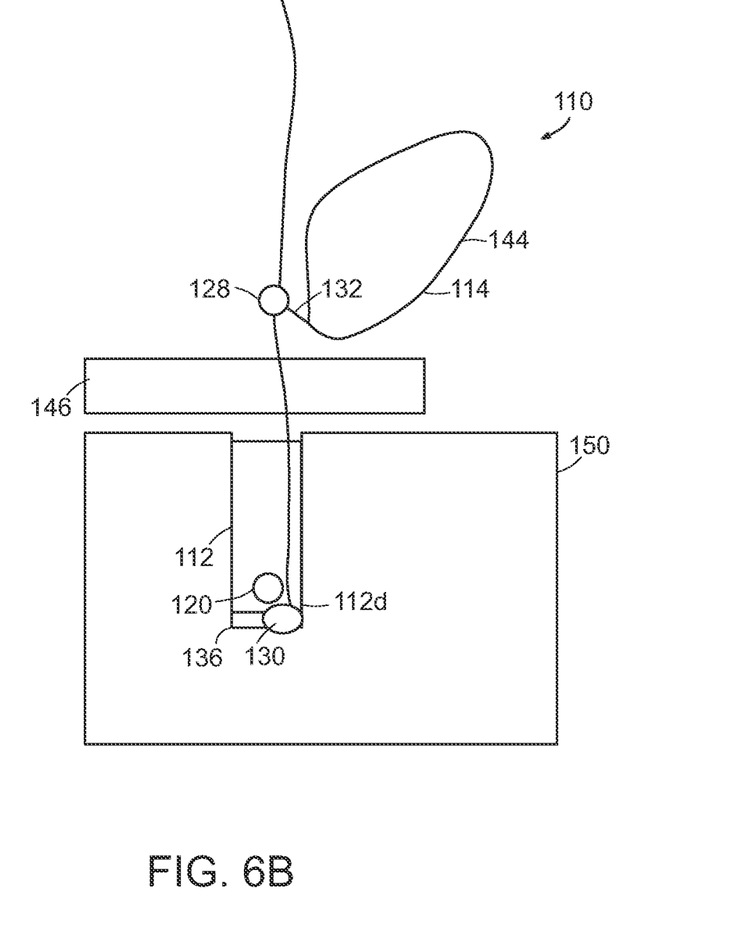
FIG. 6b is a side cross-sectional schematic view of the tissue fixation and repair construct of FIG. 5 during a subsequent step in a surgical procedure in which a portion of the construct is passed through a soft tissue.
Figure 6C:
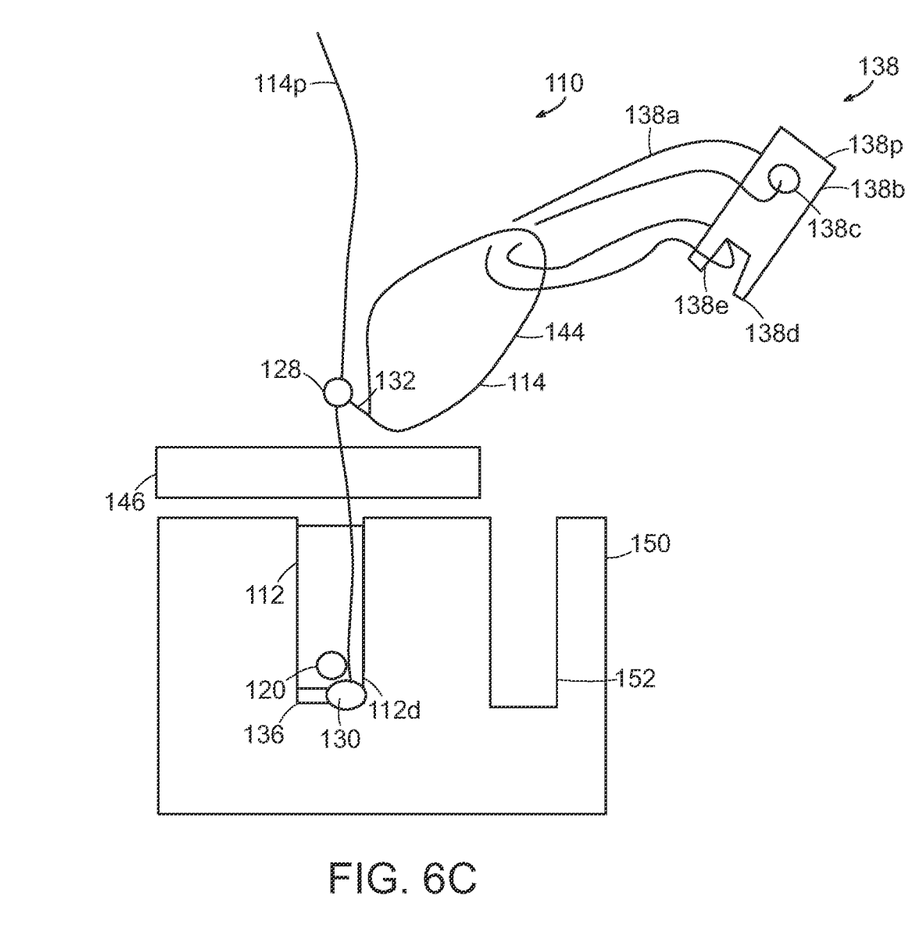
FIG. 6c is a side cross-sectional schematic view of the tissue fixation and repair construct of FIG. 5 during a subsequent step in a surgical procedure in which a second hole is formed in bone.
Figure 6D:
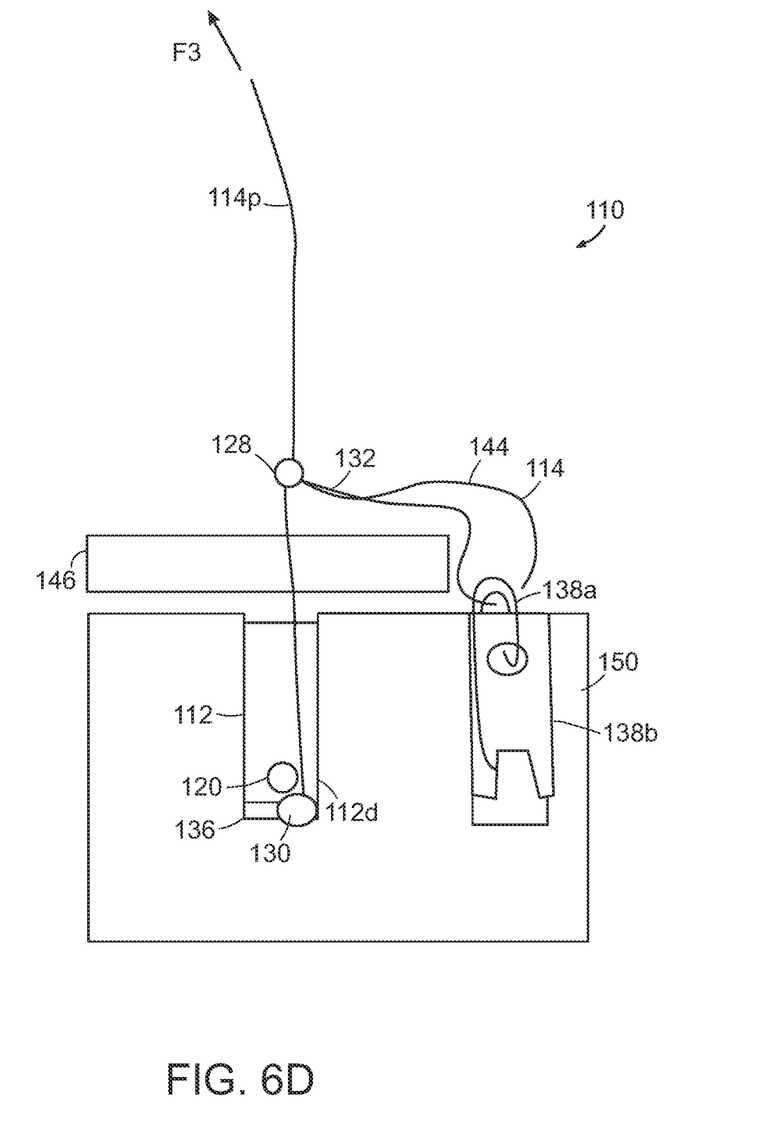
FIG. 6d is a side cross-sectional schematic view of the tissue fixation and repair construct of FIG. 5 during a subsequent step in a surgical procedure in which the second anchor is implanted into the second hole.

In another embodiment illustrated in FIGS. 5-6d, also useful in a double-row fixation repair, a tissue fixation and repair construct 110 includes a first implantable anchor 112 and a pre-spliced suture loop 114 attached thereto. The first implantable anchor 112 can be the same as or similar to first implantable anchor 12 described above and, as such, can include a lumen 118 that can be the same as or similar to the lumen 18, and an engagement feature 120 that can be the same as or similar to the first flexible member engagement feature 20. The pre-spliced suture loop 114 can be attached at its distal end 114d to the first implantable anchor 112. By way of example the distal end 112d can have a fixed stopper knot 130, similar to fixed stopper knot 30, for maintaining engagement between the pre-spliced suture loop 114, and particularly its distal end 114d, and the first implantable anchor 112, and thus prevent movement of the distal end 114d through the lumen 118. The pre-spliced suture loop 114 can include a spliced region 132 through which the pre-spliced suture loop 114 is threaded through itself to thereby form a loop 144. The loop 144 can be adjusted (i.e., closed) by pulling on a proximal end 114p of the pre-spliced suture loop 114 in the direction of arrow F3. The flexible member 114 can also include an overhand knot 128 formed thereon, which is located distally adjacent to the spliced region 132 relative to the first implantable anchor 112, such that the overhand knot 28 substantially abuts the spliced region 132. The overhand knot 128 is configured to help maintain the integrity of the spliced region 132, and to enable a portion of the flexible member 114 to pass through the overhand knot 128 in such a way that the portion can be slidably moved through the overhand knot 128 in response to tension applied by a surgeon in the direction of arrow F3. A person skilled in the art will appreciate that although a small gap may exist between the overhand knot 128 and the spliced region 132 such that the overhand knot 128 does not abut the spliced region 132 so as to be in direct contact with the spliced region 132, the overhand knot 128 can nevertheless be considered to substantially abut the spliced region 132 due to any number of facts, such as manufacturing tolerance. Although the overhand knot 128 is shown and described as an overhand knot, which may be beneficial in surgical procedures due to its low profile, any type of knot known to one of ordinary skill in the art that is capable of achieving the functionality described herein may also be used in lieu of an overhand knot, such as a hitch knot. The overhand knot 128 is formed by the flexible member 114 itself. However, in other embodiments, another flexible member can be attached to the flexible member 114 to form the overhand knot 128 (e.g., tied around the flexible member 114 to form the overhand knot 128 thereon).

An exemplary method of fixing soft tissue, such as a tendon 146, using the tissue fixation and repair construct 110 is described with reference to FIGS. 6a-6d. Similar to the method described above and illustrated in FIGS. 2a-2g, the method illustrated in FIGS. 6a-6d can be performed in a minimally invasive manner, e.g., arthroscopically, through a cannula (not shown) that can be disposed through a patient's skin. A person skilled in the art will recognize other ways by which the procedures described herein can be performed, including through three or more cannulas, a single cannula, or through no cannula at all. Further, other types of procedures, such as open procedures, can be used in conjunction with the present disclosures, which may not require a cannula.

FIG. 6a shows the tissue fixation and repair construct 110, wherein the first implantable anchor 112 has been inserted into a first bone hole 136 formed in a portion of a bone 150. While the first implantable anchor 112 and a portion of the pre-spliced suture loop 114 are disposed within the bone hole 136 and the subject's body, the remainder of the pre-spliced suture loop 114 extends through a cannula (not shown) and out of the subject's body. A portion of the pre-spliced suture loop 114 is passed through or around the tendon 146 after the first implantable anchor 112 has been inserted into the first bone hole 136, as shown in FIG. 6b. Subsequently, a second bone hole 152 is then formed in a portion of bone 150 adjacent to the first bone hole 136, as shown in FIG. 6c. The loop 144 of the pre-spliced suture loop 114 is then coupled to a coupling suture 138a of an implantable anchor assembly 138. The coupling suture 138a is coupled to a second implantable anchor 138b at an eyelet 138c located at a proximal end 138p of the second implantable anchor 138b, and at a first prong 138e at a distal end 138d. After being coupled to the loop 144, the second implantable anchor 138b is then inserted into the second bone hole 152, as shown in FIG. 6d. The pre-spliced suture loop 114 is then tensioned by pulling on the proximal end 114p of the pre-spliced suture loop 114, which collapses the loop 144 and tensions the coupling suture 138a. As the coupling suture 138a is tensioned, the second implantable anchor 138b is rotated in the second bone hole 152, such that the first prong 138e engages the walls of the second bone hole 152 to lock the second implantable anchor 138b in the second bone hole 152, thereby anchoring the tendon 146 in place. An exemplary embodiment of such a second implantable anchor, which can be used in conjunction with the constructs and relating teachings provided for herein, includes a Bioknotless RC Suture Anchor, which is commercially available from DePuy Mitek, Inc.

With each of these configurations, the tissue fixation and repair constructs 10, 110 can be tensioned after both the first implantable anchors 12, 112 and the second implantable anchors 38, 138b have been fully inserted into their respective bone holes.

Figure 7:
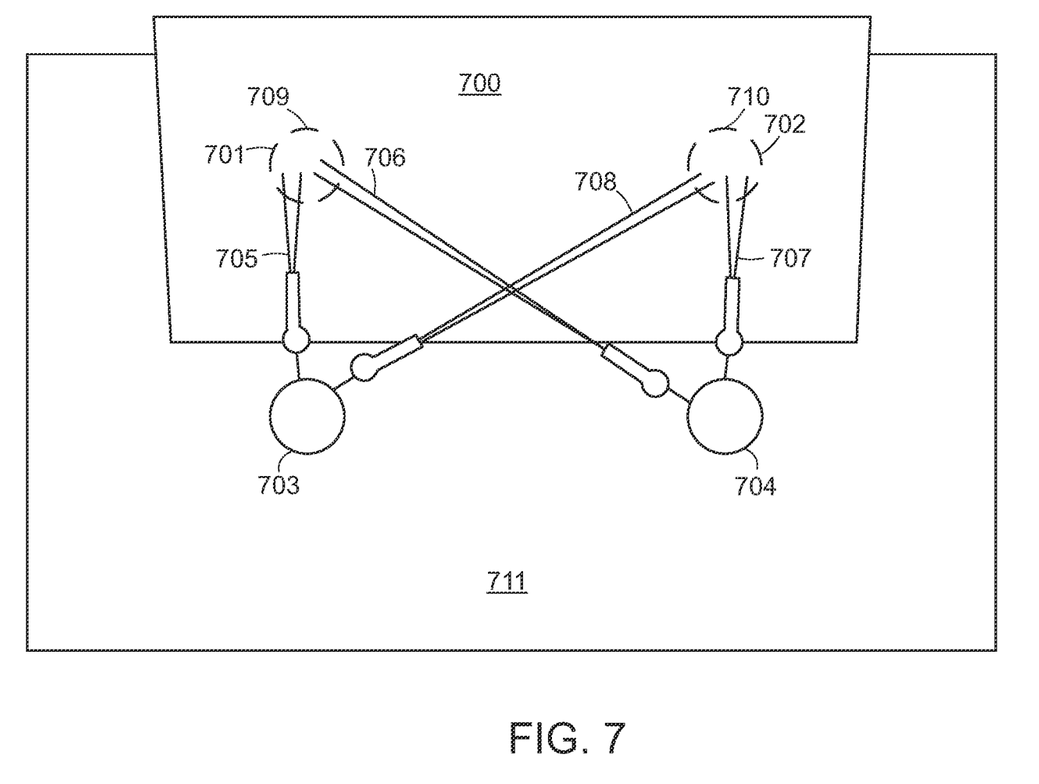
FIG. 7 is an overhead schematic view of an exemplary embodiment of a double row rotator cuff repair according to techniques disclosed herein.

Although the constructs and fixation methods described above are shown with respect to a tissue fixation and repair construct having two implantable anchors and at least one flexible member, other configurations featuring additional implantable fixed using methods similar to those described above with respect to the embodiments of FIGS. 1-2g and 5-6d. For example, FIG. 7 illustrates a double row repair in which four implantable anchors (two medial row and two lateral row) and four flexible members are used to secure a tendon 700. As shown in FIG. 7, first and second medial implantable anchors 701, 702 and first and second lateral implantable anchors 703, 704, each of which can be substantially the same as the first and second implantable anchors 12, 38, are provided. It is understood, however, that a different anchor type, such as the anchor shown in FIGS. 5-6d, can be used for the lateral row as compared to the medial row. First, second, third, and fourth flexible members 705-708 are also provided, each of which can be substantially the same as the flexible member 14 (or 114) and each of which having the same structural features as flexible member 14 (or 114) described above, are provided and can be inserted into bone holes formed in a portion of bone 711 in a similar manner to the first and second implantable anchors 12, 38. As shown, the first and second flexible members 705, 706 are coupled to the first medial implantable anchor 701 to form a first double construct 709, and the third and fourth flexible 707, 708 are coupled to the second medial implantable anchor 702 to form a second double construct 710. The first and second medial implantable anchors 701, 702 can be installed into the bone 705 in a manner similar to the first implantable anchor 12 and flexible member 14 as described above. The flexible members 705-708 can then be passed through the tendon 700 in a manner similar to that described above with respect to flexible member 14. The first lateral implantable anchor 703 can be loaded onto the first and fourth flexible members 705, 708 and the second lateral implantable anchor 704 can be loaded onto the second and third flexible members 706, 707. This loading results in a criss-cross flexible member pattern that provides enhanced support and fixation. The first and second lateral implantable anchors 703, 704 can then be installed into the bone 705, each across from the first and second medial implantable anchors 701, 702 respectively, and the first through fourth flexible members 705-708 can be tensioned in a manner similar to the tensioning of the flexible anchor 14, thereby securing the tissue in place.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method, comprising:
   inserting a tissue repair construct into a first bone hole, the tissue repair construct including a first implantable anchor having an engagement member and at least one bone engaging feature on an outer sidewall thereof, and a flexible member coupled to the engagement member, wherein the flexible member is spliced to itself to form a loop proximal to the first implantable anchor, wherein the flexible member has an intermediate portion coupled to the engagement member, with first and second tails extending therefrom, each of which having a terminal end, and wherein the flexible member is spliced by passing the first tail through a portion of the second tail;
   passing at least a portion of the flexible member through or around soft tissue;
   separating the terminal end of the first tail from the second tail;
   coupling the flexible member to a second implantable anchor, wherein the coupling of the flexible member to the second implantable anchor includes inserting the terminal end of the second tail into the second implantable anchor;
   inserting the second implantable anchor and at least a portion of the flexible member into a second bone hole; and
   tensioning the flexible member after the second implantable anchor is inserted into the second bone hole so as to apply and set a desired amount of tension in the tissue repair construct, wherein the flexible member has an intermediate portion coupled to the engagement member with first and second tails extending therefrom, each of which having a terminal end and wherein the flexible member is spliced by passing the first tail through a portion of the second tail, separating the terminal end of the first tail from the second tail, and wherein the coupling of the flexible member to the second implantable anchor includes inserting the terminal end of the second tail into the second implantable anchor.

2. The method of claim 1, wherein the second tail of the flexible member contains a first knot formed thereon and a hollow portion forming an interior collapsible passage, the first knot being located distal of and adjacent to the hollow portion.

3. The method of claim 1, wherein the second tail of the flexible member contains a fixed knot spaced from the hollow portion.

4. The method of claim 3, wherein the second implantable anchor is disposed proximate the fixed knot.

5. The method of claim 1, wherein the intermediate portion is slidably coupled to the engagement member.

6. The method of claim 1, wherein the terminal end of the first tail is configured to be coupled to the second tail.

7. The method of claim 1, wherein a distal end of the flexible member is coupled to the first implantable anchor and wherein the second implantable anchor is coupled to the first implantable anchor by coupling the loop in the flexible member to a coupling suture attached to the second implantable anchor.

* * * * *